US009624315B2

(12) United States Patent
Guo et al.

(10) Patent No.: US 9,624,315 B2
(45) Date of Patent: Apr. 18, 2017

(54) PREPARATION OF NEW INTERMEDIATE OF HEPARIN PENTASACCHARIDE AND PREPARATION METHOD THEREOF

(71) Applicant: Zhejiang Hisun Pharmaceutical Co., Ltd., Taizhou (CN)

(72) Inventors: Yanghui Guo, Taizhou (CN); Hegeng Wei, Taizhou (CN); Hua Bai, Taizhou (CN); Yingqiu Wu, Taizhou (CN); Yue Zhang, Taizhou (CN); Junhui Zhou, Taizhou (CN); Yili Ding, Taizhou (CN); Lingwei Bai, Taizhou (CN); Shibao Yang, Taizhou (CN)

(73) Assignee: Zhejiang Hisum Pharmaceutical Co., Ltd. (CN)

( * ) Notice: Subject to any disclaimer, the term of this patent is extended or adjusted under 35 U.S.C. 154(b) by 225 days.

(21) Appl. No.: 14/389,806

(22) PCT Filed: Apr. 2, 2013

(86) PCT No.: PCT/CN2013/073601
§ 371 (c)(1),
(2) Date: Oct. 1, 2014

(87) PCT Pub. No.: WO2013/149576
PCT Pub. Date: Oct. 10, 2013

(65) Prior Publication Data
US 2015/0299340 A1 Oct. 22, 2015

(30) Foreign Application Priority Data
Apr. 2, 2012 (CN) .......................... 2012 1 0102415

(51) Int. Cl.
*C07H 11/00* (2006.01)
*C07H 5/06* (2006.01)
*C07H 15/18* (2006.01)
*C08B 37/00* (2006.01)
*C07H 1/00* (2006.01)
*C07H 15/04* (2006.01)

(52) U.S. Cl.
CPC .......... *C08B 37/0075* (2013.01); *C07H 1/00* (2013.01); *C07H 5/06* (2013.01); *C07H 11/00* (2013.01); *C07H 15/04* (2013.01); *C07H 15/18* (2013.01); *C08B 37/006* (2013.01)

(58) Field of Classification Search
None
See application file for complete search history.

(56) References Cited

U.S. PATENT DOCUMENTS

| 4,841,041 | A | 6/1989 | van Boeckel et al. |
| 2005/0080042 | A1 | 4/2005 | Seifert et al. |

FOREIGN PATENT DOCUMENTS

| JP | 6440492 | | 2/1989 |
| JP | 2005505565 | A | 2/2005 |
| WO | 03022860 | A1 | 3/2003 |
| WO | 2010037179 | A1 | 4/2010 |
| WO | 2010040880 | A1 | 4/2010 |

OTHER PUBLICATIONS

Manikowski et al., "An alternative route for fondaparinux sodium synthesis via selective hydrogenations and sulfation of appropriate pentasaccharides" Carbohydrate Research (2012) vol. 361 pp. 155-161.*
Van Boeckel et al., "Synthesis of a potnet antithrombin activating pentasaccharide: A new heparin-like fragment containing two 3-O-sulphated glucosamines" Tetrahedron Letters (1988) vol. 29 No. 7 pp. 803-806.*
Aelst et al., "Synthesis of an analog of the antithrombin binding region of heparin containing .alpha.-L-idopyranose" Recueil des travaux chimiques des Pays-Bas (1987) vol. 106 No. 11 pp. 593-595.*
Boeckel et al., "Synthesis of a Pentasaccharide Corresponding to the Antithrombin III Binding Fragment of Heparin", Journal of Carbohydrate Chemistry, Mar. 4, 1985, 4(3), pp. 293-321.
Hirsh et al., "Low Molecular Weight Heparin", Blood, The Journal of the American Society of Hematology, Jan. 1, 1992, vol. 79, No. 1, pp. 1-17.
Howell, "The Purification of Heparin and Its Chemical and Physiological Reactions", Bulletin of the Johns Hopkins Hospital, Jan. 19, 1928, vol. 42, No. 4, pp. 199-206.
International Search Report for Application No. PCT/CN2013/073601 dated Jul. 11, 2013.
Linhardt, "Heparin: An Important Drug Enters Its Seventh Decade", Chemistry and Industry, Jan. 21, 1991, 2, pp. 45-50.
Petitou et al., "Synthesis of Heparin Fragments . . . ", Carbohydrate Research, 1986, 147, pp. 221-236.
Petitou et al., "Synthesis of Heparin Fragments: A Methyl Pentaoside With High Affinity for Antithrombin III*"Carbohydrate Research, 1987, 167, pp. 67-75.
Sinay et al., "Total synthesis of a heparin pentasaccharide fragment having high affinity for antithrombin III", Carbohydrate Research, 132, (1984), pp. C5-C9.
Christian Noti et al: "Preparation and Use of Microarrays Containing SyntheticHeparin Oligosaccharides for the Rapid Analysis of Heparin-Protein Interactions" Chemistry—A European Journal, vol. 12 No. 34, Nov. 24, 2006 (Nov. 24, 2006)8664-8686,XP055005794 ISSN: 0947-6539, DOI: 10.1002/chem.200601103 * p. 8664 right-hand column, lines 5-15 * left-hand column last sentence to right-hand column line 18; p. 8667 * * Scheme 5 compounds 24 and 25; p. 8668 *.
Extended European Search Report for Application No. EP13772346 dated Apr. 29, 2015.
Lu Lung-Dai, et al., Synthesis of 48 Disaccharide Building Blocks for the Assembly of a Heparin and Heparan Sulfate Oligosaccharide Library, Organic Letters, 2006, vol. 8, No. 26, pp. 5995-5998, S36-39.
Kiyoshi Tomioka, Strategic Applications of Named Reactions in Organic Synthesis, Kagaku-Dojin Publishing Co., Inc., Aug. 15, 2006, first edition, first printing, p. 428 through p. 429.

* cited by examiner

*Primary Examiner* — Eric Olson
(74) *Attorney, Agent, or Firm* — Lerner, David, Littenberg, Krumholz & Mentlik, LLP

(57) ABSTRACT

The present invention relates to a process of a chemically synthetic drug, and in particular, to a new intermediate of a heparin pentasaccharide and a preparation method thereof. The process has high reaction efficiency, and an easy reaction operation. The reaction intermediate is easy to be purified, and is appropriate for an industrialization production.

18 Claims, 3 Drawing Sheets

PREPARATION OF NEW INTERMEDIATE OF HEPARIN PENTASACCHARIDE AND PREPARATION METHOD THEREOF

CROSS-REFERENCE TO RELATED APPLICATIONS

The present application is a national phase entry under 35 U.S.C. §371 of International Application No. PCT/CN2013/073601, filed on Apr. 2, 2013, published in Chinese, which claims priority from Chinese Patent Application No. 201210102415.0, filed Apr. 2, 2012, the disclosures of which are hereby incorporated herein by reference.

FIELD OF THE INVENTION

The present invention relates to the field of chemical synthesis, in particular, relates to a preparation method for converting fully protected heparin pentasaccharide precursor into heparin pentasaccharide.

BACKGROUND OF THE INVENTION

Heparin was firstly isolated from animal livers by Jay McLean of Johns Hopkins University in 1916, and was identified to be the active ingredient in anti-coagulation (a: Chem. Ind. 1991, 2, 45-50; b: Bull. Johns Hopkins Hosp. 1928, 42, 199), and among glycosaminoglycan (GAG) family, it has the most complex structure. Heparin has been used in clinical treatment of anti-thrombosis and cardiovascular diseases for nearly 60 years, and among its physical activities, the activity in anti-coagulation has been studied and illustrated most intensively and has promoted the use of low molecular heparin (LMWH) as a general anticoagulant, as the substitute of conventional clinical anticoagulants, since 1990's (Blood, 1992, 79, 1-17). Blood coagulation is the consequent of sequential activation of a series of coagulation factors in blood plasma. Finally, inactive thrombin is converted into active thrombin, soluble fibrinogen is partly hydrolyzed and insoluble fibrin is released, resulting in the coagulation of blood. Antithrombin III (ATIII) is the inhibitor of serine protease, in particular thrombin IIa and Xa, in blood coagulation. Although antithrombin III is reacted with thrombin slowly, the reaction rate will increase by thousands of times in the presence of heparin, such that blood coagulation can be inhibited effectively. Natural heparin is mainly extracted from animal viscera and is a complex mixture consisting of different active polysaccharides, and thus its effective dosage cannot be controlled effectively during its application, which may result in risky adverse effects, such as blooding, thrombocytopenia, etc. Meanwhile, heparin molecule may non-specifically bind with blood plasma proteins, resulting in more complex complications. At the end of 1980's, the occurrence of low molecular heparin (LMWH) improves the therapeutic effects of anti-thrombosis. Low molecular heparin is obtained from intact heparin by chemical degradation, enzyme degradation, and gamma-radiation degradation. The trouble is, since their animal sources, heparin and low molecular heparin has the risk of cross virus infection by various species, rendering its application very risky. The most effective means for avoiding such cross virus infection by various species is chemical synthesis of heparin.

Fondaparinux sodium, with chemical name of methyl O-(2-deoxy-6-O-sulfo-2-sulfoamino-α-D-glucopyranosyl)-(1→4)-O-(β-D-glucopyranuronosyl)-(1→4)-O-(2-deoxy-3,6-di-O-sulfo-2-sulfoamino-α-D-glucopyranosyl)-(1→4)-O-(2-O-sulfo-α-L-idopyranuronosyl)-(1→4)-2-deoxy-6-O-sulfo-2-sulfoamino-α-D-glucopyranoside, decasodium salt, belongs to heparin pentasaccharide and was commercialized as anticoagulant in 2001. Its chemical structure is presented in formula 10 as follows:

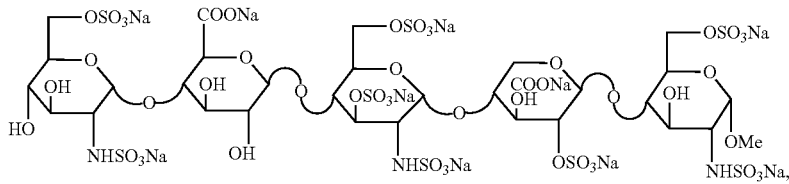

Fondaparinux Sodium

In the middle of 1980's, Sinay et. al (Carbohydr. Res. 1984, 132, C5-C9, Carbohydr. Res. 1986, 147, 221-236) and Boeckel et. al (J. Carbohydr. Chem. 1985, 4, 293-321.) successively achieved the fully synthesis of anticoagulant pentasaccharide without capped methyl. Fully protected pentasaccharide is converted into the final product pentasaccharide via the reaction schemes represented by the following formulae 1-5. The reaction steps includes: 1. saponification of the ester group, 2. sulfation of the hydroxyl group, 3. hydrogenation reduction of azido or carboxybenzyl-protected amino group to unprotected amino group with Pd/C, and subsequent deprotection of benzyl protective group on hydroxyl group, and 4. selective sulfation of amino group.

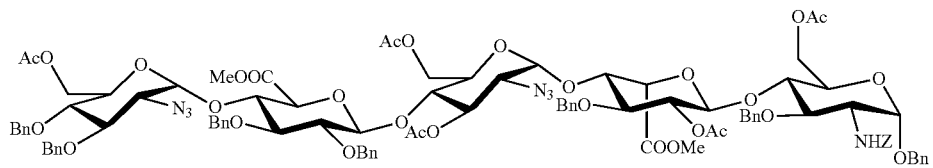

1

↓

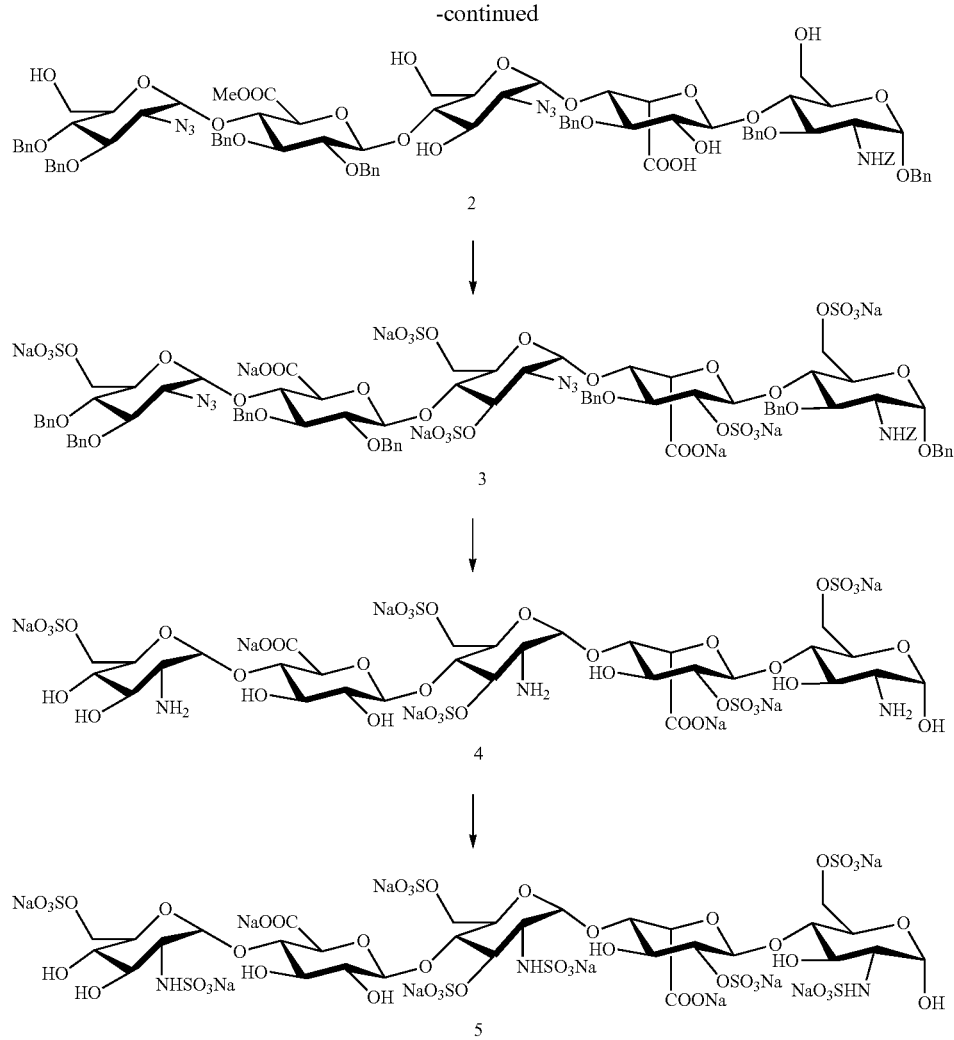

In the above mentioned conversion of the pentasaccharide, the reduction of azido group to amino group is very rapid, and it tends to successively carry out adverse reaction with reductive terminal aldehyde group of the hemiacetal tautomer of the pentasaccharide, generating stable dimmers or trimers, resulting in extremely poor reaction efficiency.

In the process of resolving the problem, it is found that the problem of the formation of dimmers and trimers during the reduction in the synthesis process can be avoided by using methyl-capped pentasaccharide (Carbohydr. Res. 1987. 167, 67-75), such that the hydrogenation reduction can be carried out with nearly quantitative yield, with a reaction scheme as presented in following scheme 6-10. Its synthesis scheme is substantially identical to that using uncapped pentasaccharide as the raw material, and includes the following 4 steps: 1. saponification of the ester group of the fully protected pentasaccharide, generating five unprotected hydroxyl groups to be subjected to sulfation, 2. sulfation of the hydroxyl group, 3. hydrogenation reduction of azido-protected or benzylcarbonyl-protected amino group to unprotected amino group with Pd/C, and subsequent deprotection of hydroxyl group, and 4. selective sulfation of amino group, in order to obtain the product fondaparinux sodium.

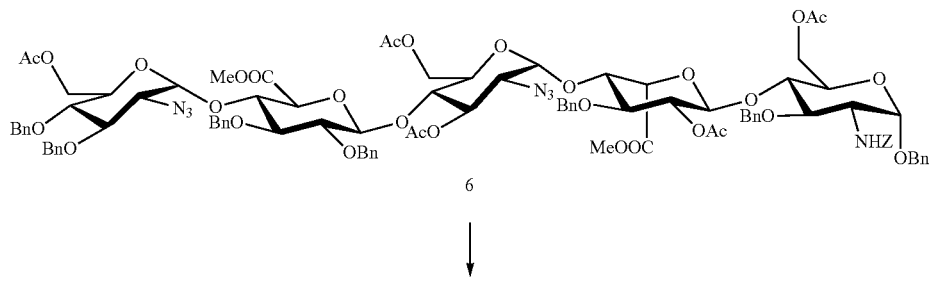

-continued

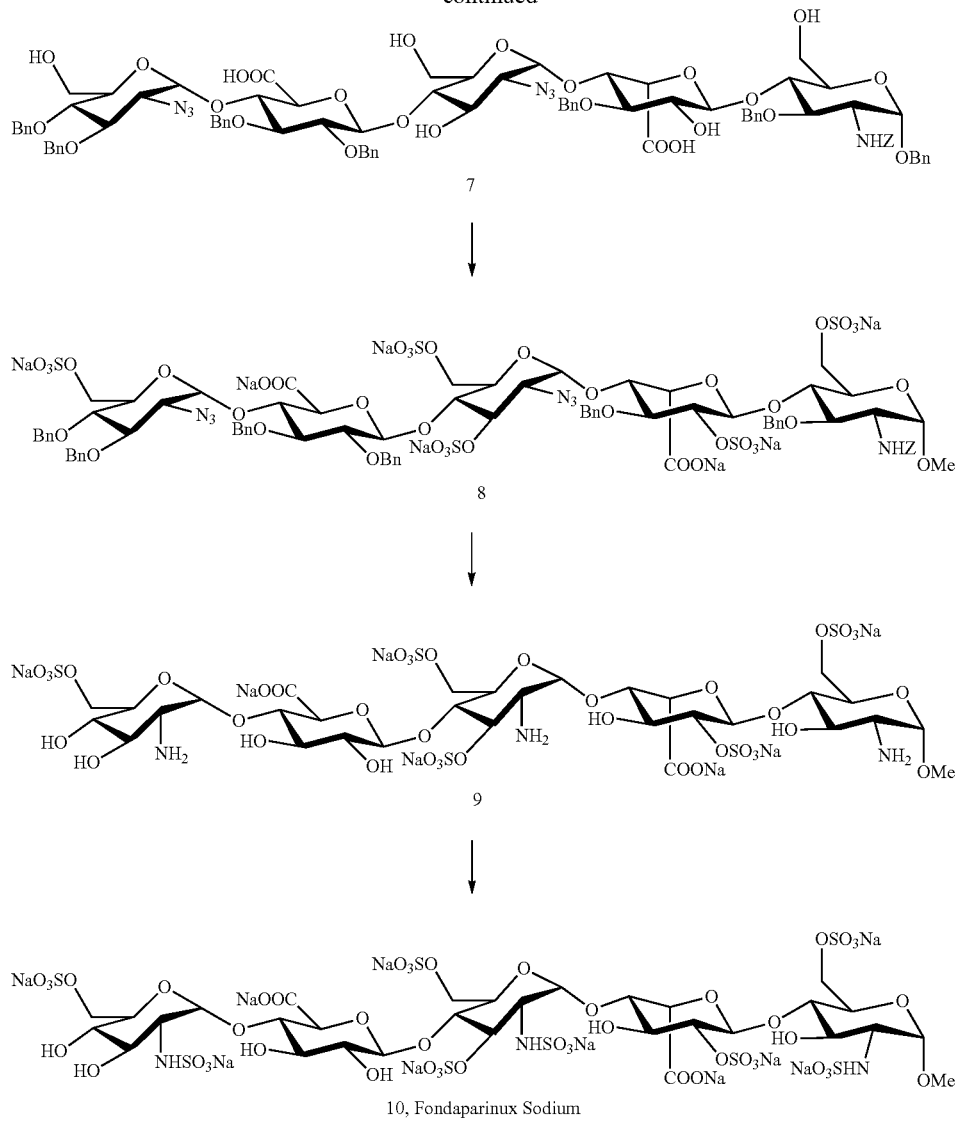

10, Fondaparinux Sodium

WO2003022860 and WO2010040880 also employ similar method.

Tests on biological activity demonstrate that, methyl protection of reduction terminal has no influence on the biological activity of heparin pentasaccharide, and thus the protection strategy using methyl capping becomes a routine strategy for the synthesis of heparin oligomeric molecules.

The method according to the prior art requires simultaneous conversion of benzyl-protected hydroxyl and azido (or benzoxylcarboxyl-protected amino) into unprotected hydroxyl and amino via hydrogenation, wherein the intermediate has poor stability and is hard to be purified. Furthermore, the final step requires selective sulfation of all three amino groups among six unprotected hydroxyl and three unprotected amino. The yield of the reaction is very poor, due to poor selectively of the reaction, and the final product is hard to be purified.

The process according to the present invention employs a highly efficient reduction process to reduce azido group into unprotected amino group firstly, after removing the ester group of fully protected pentasaccharide. The crude intermediate has high purity, and can be used in the next step without purification. Subsequently, all of unprotected hydroxyl groups and amino groups are sulfated. It has high efficiency, and the remaining benzyl group facilitates the purification of such intermediate. Finally, all of the benzyl groups are removed via hydrogenation, in order to obtain the final product.

DESCRIPTION OF THE INVENTION

The present invention provides a process for converting a fully protected heparin pentasaccharide intermediate into heparin pentasaccharide, and also provides a new intermediate.

One object of the present invention is to provide a compound having the following formula I, which can be used as an intermediate for the preparation of heparin pentasaccharide,

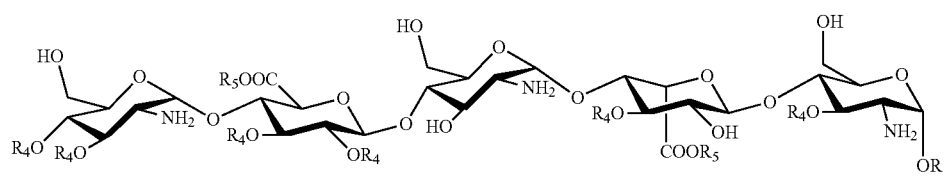

wherein the configuration of monosaccharide units and the stereochemistry of the connecting bond among each of the monosaccharide is D-glucosyl-α-1,4-D-glucuronosyl-β-1,4-D-glucosyl-α-1,4-L-idoronosyl-α-1,4-D-glucose, wherein the definition of each substituent is as follows.

R represents $C_1$-$C_{20}$ alkyl or substituted alkyl, wherein the alkyl can be either linear alkyl or branched or cyclic alkyl, such as methyl, ethyl, propyl, isopropyl, butyl, isobutyl, tert-butyl, pentyl, cyclohexyl, etc., and the substituted alkyl can be benzyl, allyl, methoxymethyl, or 2-methoxyethyl, etc., preferably, R is methyl.

$R_4$ represents benzyl or substituted benzyl, wherein substituted benzyl can be p-methoxybenzyl, triphenylmethyl, etc., $R_4$ in the same molecular formula represents either identical group or different group.

$R_5$ represents hydrogen ion or alkali metal ion, the alkali metal ion is preferably sodium ion.

Another object of the present invention is to provide a compound represented by the following structure II, which can be used as an intermediate for the preparation of heparin pentasaccharide,

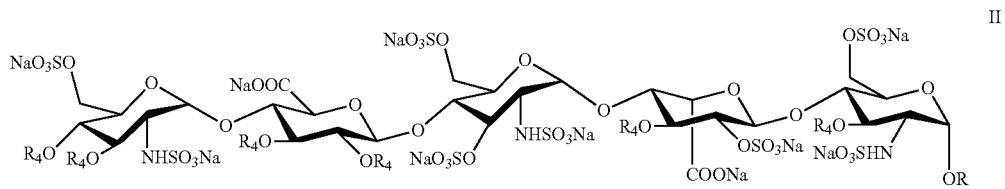

wherein the configuration of monosaccharide units and the stereochemistry of the connecting bond among each of the monosaccharides is D-glucosyl-α-1,4-D-glucuronosyl-β-1,4-D-glucosyl-α-1,4-L-idoronosyl-α-1,4-D-glucose, wherein the definition of each substituent is as follows.

R represents $C_1$-$C_{20}$ alkyl or substituted alkyl, wherein the alkyl can be either linear alkyl or branched or cyclic alkyl, such as methyl, ethyl, propyl, isopropyl, butyl, isobutyl, tert-butyl, pentyl, cyclohexyl, etc., and the substituted alkyl can be benzyl, allyl, methoxymethyl, or 2-methoxyethyl, etc., preferably, R is methyl.

$R_4$ represents benzyl or substituted benzyl, wherein substituted benzyl can be p-methoxybenzyl, triphenylmethyl, etc., $R_4$ in the same molecular formula represents either identical group or different group.

In addition to sodium salt, the compound of formula II of the present invention can be any other pharmaceutically acceptable salts, e.g. potassium salt, calcium salt, etc.

A further object of the present invention is to provide a process for the preparation of a compound of the above formula I, comprising the following steps, a) firstly, treating the fully protected pentasaccharide compound of the following formula III with sodium hydroxide,

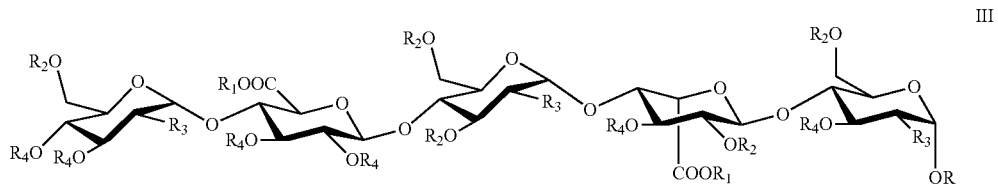

such that the compound of formula III is subjected to ester hydrolysis, in order to obtain the compound having the following formula IV wherein $R_5$ is sodium ion, alternatively, the compound is subjected to hydrolysis and subsequent acid neutralization, in order to obtain the compound having the following formula IV wherein $R_5$ is hydrogen ion,

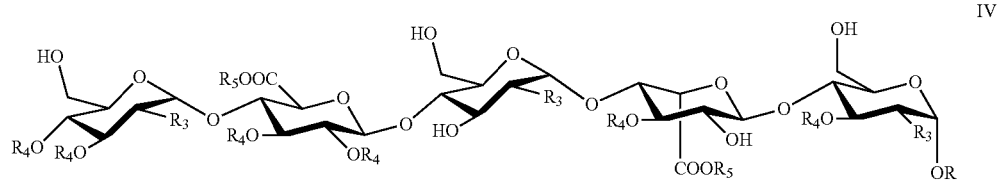

IV wherein R represents $C_1$-$C_{20}$ alkyl or substituted alkyl, wherein the alkyl can be either linear alkyl or branched or cyclic alkyl, and the substituted alkyl can be benzyl, allyl, methoxymethyl, or 2-methoxyethyl, etc.; $R_1$ represents $C_1$-$C_{20}$ alkyl, substituted alkyl, hydrogen ion, sodium ion, wherein the alkyl can be either linear alkyl or branched or cyclic alkyl, and the substituted alkyl can be benzyl, allyl, methoxymethyl, or 2-methoxyethyl, etc., $R_1$ in the same molecular formula represents either identical group or different group; $R_2$ represents linear or branched aliphatic acyl or aryl acyl, such as acetyl, 4-oxovaleryl, benzoyl, etc., $R_2$ in the same molecular formula represents either identical group or different group; $R_3$ represents azido group; $R_4$ represents benzyl or substituted benzyl, wherein substituted benzyl can be p-methoxybenzyl, triphenylmethyl, etc., $R_4$ in the same molecular formula represents either identical group or different group; $R_5$ is selected from hydrogen ion or sodium ion; wherein the acid is preferably hydrochloric acid;

b) secondly, treating the compound of formula IV with a reductant, i.e. the group $R_3$ is reduced to amino group, in order to obtain the compound of formula I.

Wherein the compound of formula IV for the preparation of the compound of formula I can be subjected to reduction after separation and purification, alternatively, the compound of formula IV obtained from the reaction can also be subjected to one-pot reaction process without separation and purification.

Another object of the present invention is to provide an alternative process for the preparation of the compound of above formula I, comprising the following steps:

a) firstly, treating the fully protected pentasaccharide compound of formula III with a reductant, i.e. reducing $R_3$ into amino group, in order to obtain the compound of the following formula V,

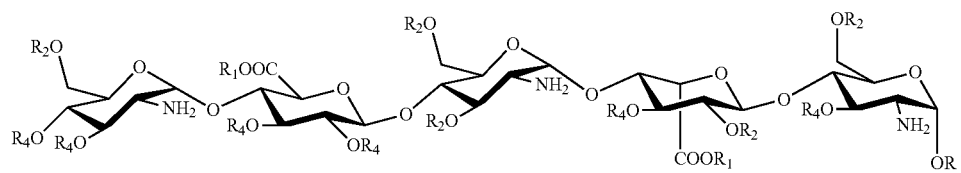

V wherein R represents $C_1$-$C_{20}$ alkyl or substituted alkyl, wherein the alkyl can be either linear alkyl or branched or cyclic alkyl, and the substituted alkyl can be benzyl, allyl, methoxymethyl, or 2-methoxyethyl, etc.; $R_1$ represents $C_1$-$C_{20}$ alkyl, substituted alkyl, hydrogen ion, sodium ion, wherein the alkyl can be either linear alkyl or branched or cyclic alkyl, and the substituted alkyl can be benzyl, allyl, methoxymethyl, or 2-methoxyethyl, etc., $R_1$ in the same molecular formula represents either identical group or different group; $R_2$ represents linear or branched aliphatic acyl or aryl acyl, such as acetyl, 4-oxovaleryl, benzoyl, etc., $R_2$ in the same molecular formula represents either identical group or different group; $R_4$ represents benzyl or substituted benzyl, wherein substituted benzyl can be p-methoxybenzyl, triphenylmethyl, etc., $R_4$ in the same molecular formula represents either identical group or different group;

b) secondly, treating the compound of formula V with sodium hydroxide, such that the compound of formula V is subjected to ester hydrolysis, in order to obtain the compound of formula I wherein $R_5$ is alkali metal ion, preferably sodium ion, alternatively, it is subjected to ester hydrolysis and subsequent acid neutralization, in order to obtain the compound of formula I wherein $R_5$ is hydrogen ion.

The reductant employed in the above mentioned processes can be selected from trimethylphosphine, triethylphosphine, tributylphosphine, triphenylphosphine, or hydrogen sulfide. Wherein the acid used is preferably hydrochloric acid.

The present invention also provides a process for the preparation of the compound of formula II, comprising treating the compound of formula I with a sulfating reagent, and treating the crude product with sodium ion exchange resin, in order to obtain the compound of formula II; wherein the sulfating reaction can be carried out in a single step or in several steps. Said single step of sulfating reaction is carried out in the presence of sulfating reagent, pyridine, and triethylamine. the sulfating reaction can also be carried out stepwise, i.e. reacting sulfating reagent with N,N-dimethylformamide under the condition of a certain temperature, such that a major of hydroxyl are sulfated, and then treating with a minor amount of sulfating reagent/pyridine/triethylamine, such that amino and a small amount of unreacted hydroxyl are sulfated. Preferably, the temperature is 50° C. Wherein, the sulfating agent is selected from sulfur trioxide-pyridine complex, sulfur trioxide-trimethylamine complex, sulfur trioxide-triethylamine complex, or gaseous sulfur trioxide.

The present invention also provides a process for the preparation of heparin pentasaccharide, comprising treating the compound of formula II with a catalyst, such as palladium hydroxide, palladium on carbon, etc., under hydrogen condition, such that all $R_4$ groups of the compound of formula II are removed, in order to obtain heparin pentasaccharide.

A particular process for the preparation of heparin pentasaccharide according to the present invention comprises the following steps:

1. subjecting the compound of formula III to ester hydrolysis in the presence of sodium hydroxide, in order to obtain the compound of formula IV;

2. reducing $R_3$ group in the compound of formula IV to amino group, in order to obtain the compound of formula I;

3. subjecting the unprotected hydroxyl and amino groups generated in step 1 and step 2 in the compound of formula I to sulfation, in order to obtain the compound of formula II; and 4. subjecting the compound of formula II to catalytic hydrogenation, in order to remove $R_4$ groups, and obtain heparin pentasaccharide of formula VI.

The conversion process is as follows:

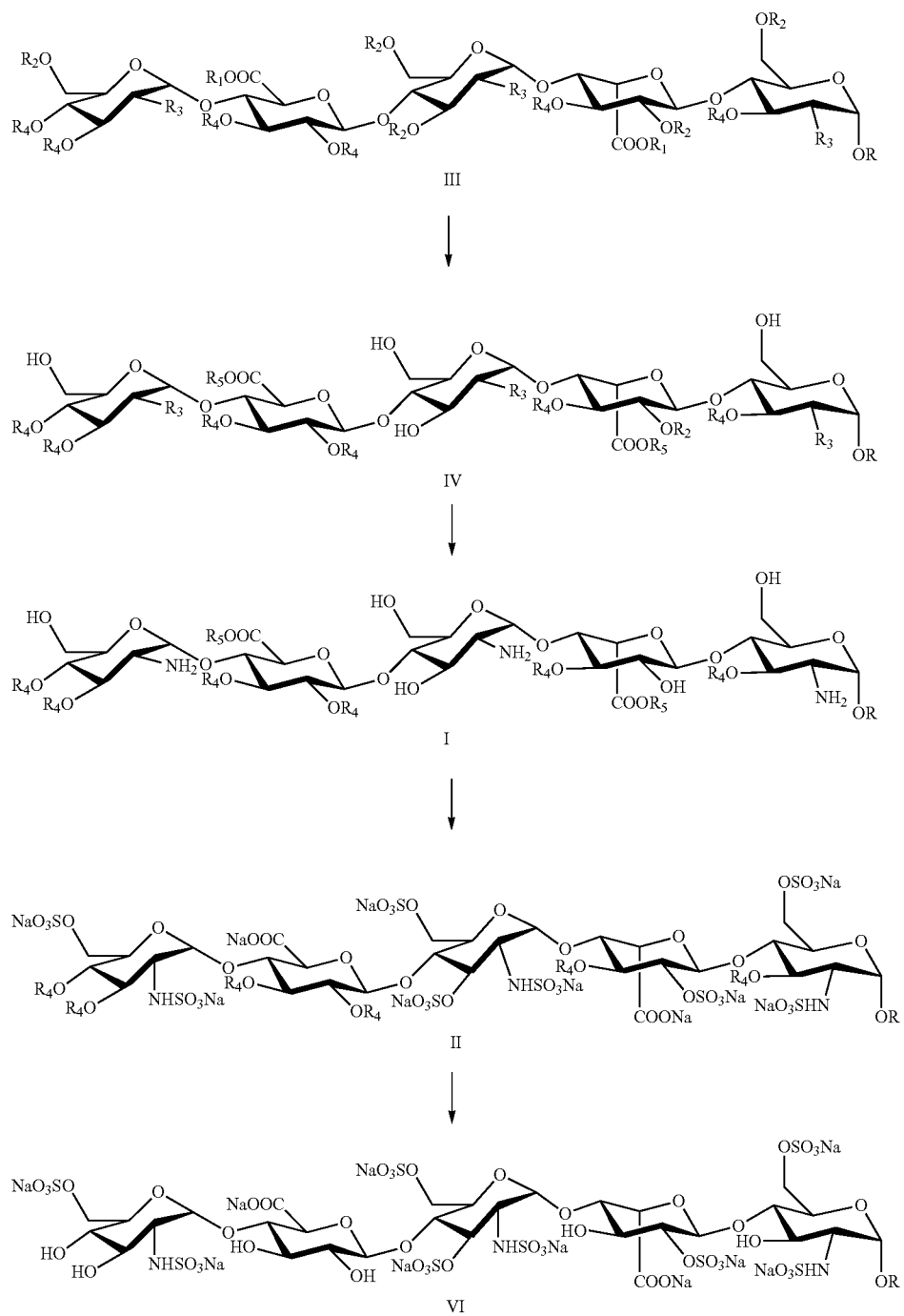

A particular process for the preparation of heparin pentasaccharide according to the present invention can also comprise the following steps:

1. reducing $R_3$ groups on the compound of formula III to amino group, in order to obtain the compound of formula V,
2. subjecting the compound of formula V to ester hydrolysis in the presence of sodium hydroxide, without separation and purification of the compound of formula V, in order to obtain the compound of formula I,
3. subjecting the unprotected hydroxyl and amino groups generated in step 1 and step 2 in the compound of formula I to sulfation, in order to obtain the compound of formula II; and
4. subjecting the compound of formula II to catalytic hydrogenation, in order to remove $R_4$ groups, and obtain heparin pentasaccharide of formula VI.

The conversion process is as follows:

The process according to the present invention has the following advantages and benefit effects:

1. The present invention employs a highly efficient reduction process to reduce azido group into unprotected amino group, such that the crude intermediate has higher purity and can be applied in the next step, without purification, which simplifies the operation.
2. The sulfation according to the present invention can fully sulfate all of the unprotected hydroxyl groups and amino groups, with higher efficiency. In particular, the selection of stepwise sulfation can reduce the amount of sulfation reagent used, and simplify the aftertreatment process, with better effects.
3. The benzyl protection strategy according to the present invention, i.e. keeping benzyl until later stage, allows easier purification of a series of intermediates, and is suitable for industrial production.

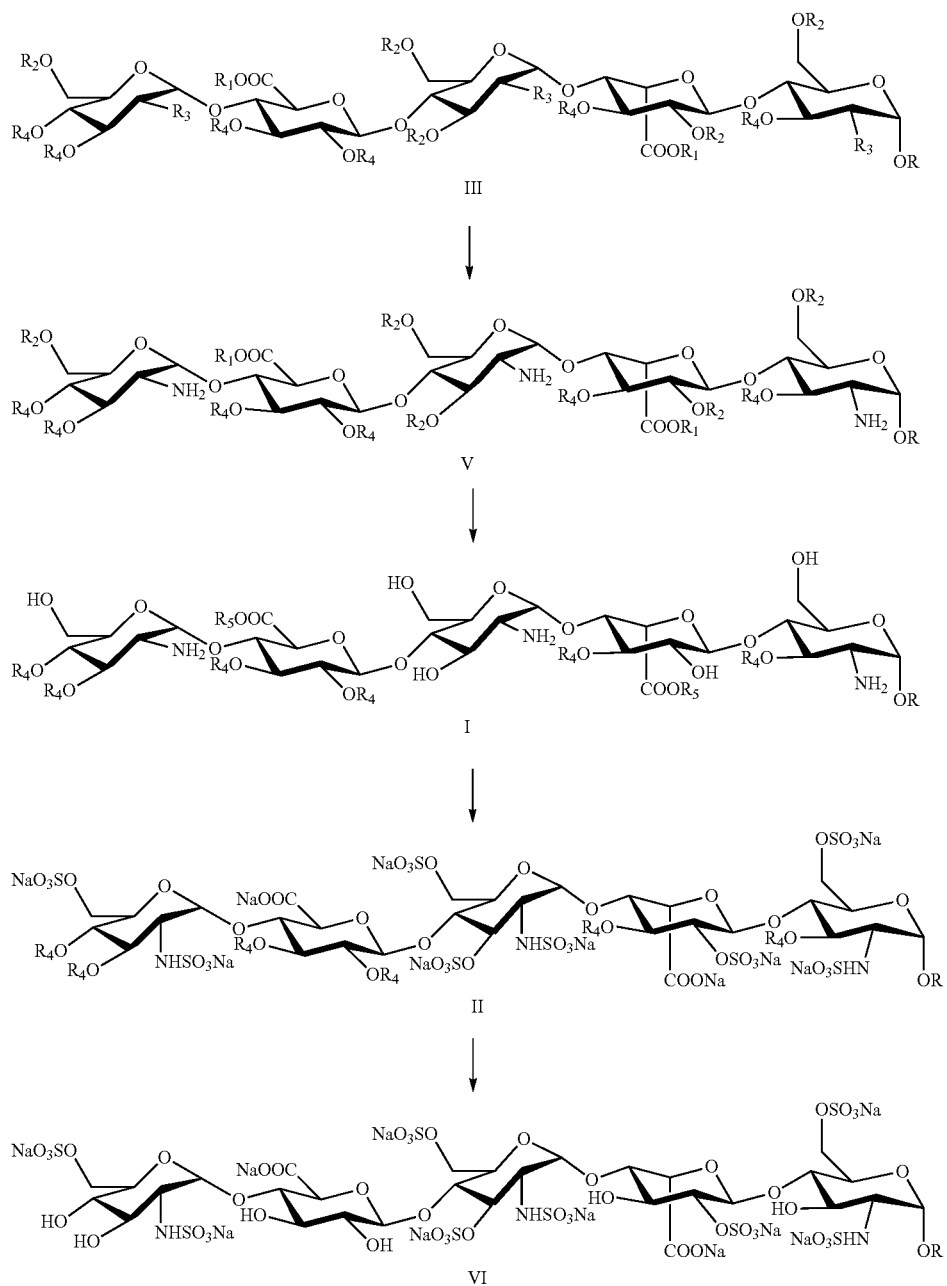

4. The final step according to the present invention, i.e. removing the protective benzyl via catalytic hydrogenation, allows easy purification of final product, and is suitable for industrial production.

EXAMPLES

Example 1

Figure 1:
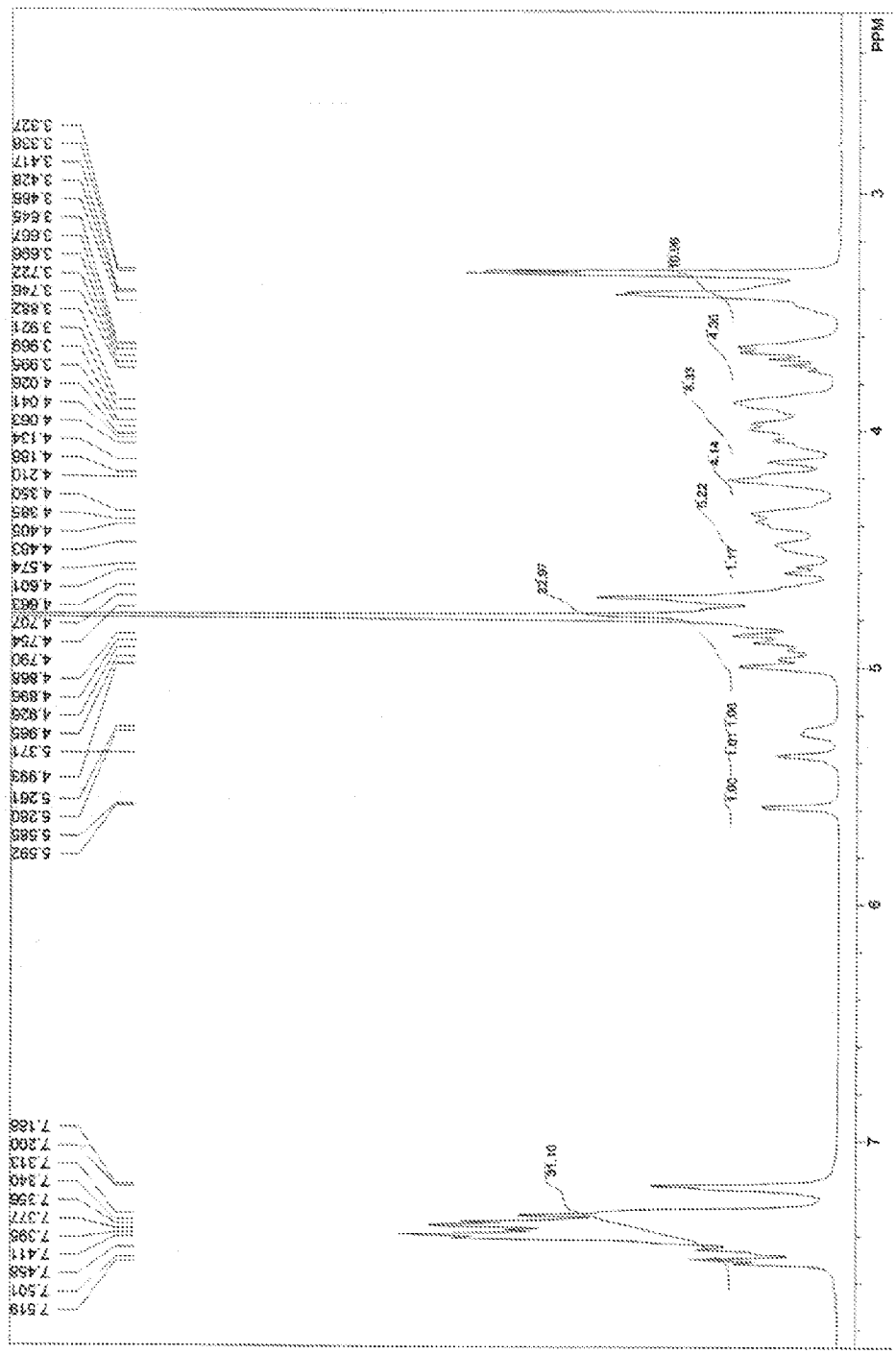
FIG. 1 is the $^1$H NMR of the compound of formula II-1 prepared according to Example 5.

Preparation of methyl O-(2-azido-3,4-di-O-benzyl-2-deoxy-α-D-glucopyranosyl)-(1→4)-O-(2,3-di-O-benzyl-β-D-glucopyranuronosyl)-(1→4)-O-(2-azido-2-deoxy-α-D-glucopyranosyl)-(1→4)-O-(3-O-benzyl-α-L-idopyranuronosyl)-(1→4)-2-azido-3-O-benzyl-2-deoxy-α-D-glucopyranoside (IV-1)

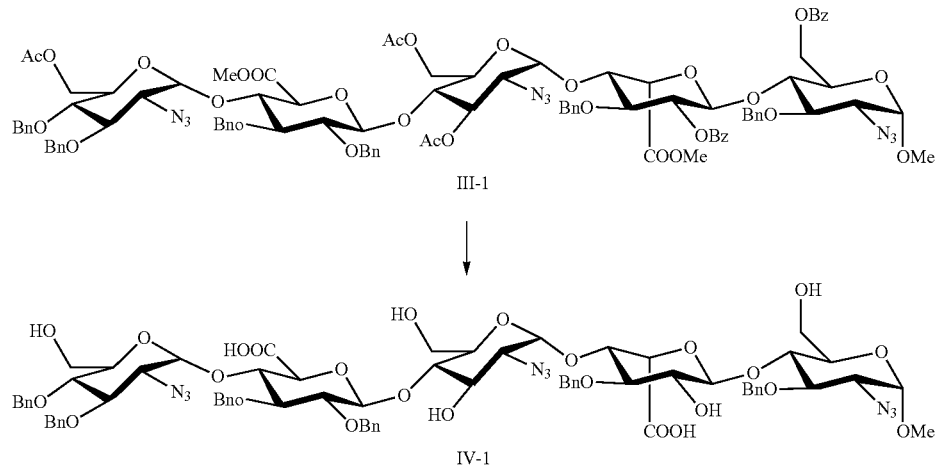

Fully protected pentascharride compound of formula III-1 (10 g, 5.4 mmol) was dissolved in tetrahydrofuran (220 mL). Aqueous solution of sodium hydroxide (110 mL, 1.0M, 20 eq., 110 mmol) was added dropwise. After the addition was completed, it was stirred overnight at room temperature, until the reaction was complete. It was then neutralized with 1 M hydrochloric acid and extracted with ethyl acetate. The organic phases were combined and were successively washed with water, 10% citric acid, saturated saline solution, and dried over anhydrous sodium sulfate, and then concentrated under reduced pressure to remove the solvent, in order to obtain 8.0 g compound of formula IV-1, in the form of foamy solid.

ESMS: m/Z=1486 [M+1]$^+$, 1484 [M−1]$^−$.

Example 2

Preparation of methyl O-(2-amino-3,4-di-O-benzyl-2-deoxy-α-D-glucopyranosyl)-(1→4)-O-(2,3-di-O-benzyl-β-D-glucopyranuronosyl)-(1→4)-O-(2-amino-2-deoxy-α-D-glucopyranosyl)-(1→4)-O-(3-O-benzyl-α-L-idopyranuronosyl)-(1→4)-2-amino-3-O-benzyl-2-deoxy-α-D-glucopyranoside (I-1)

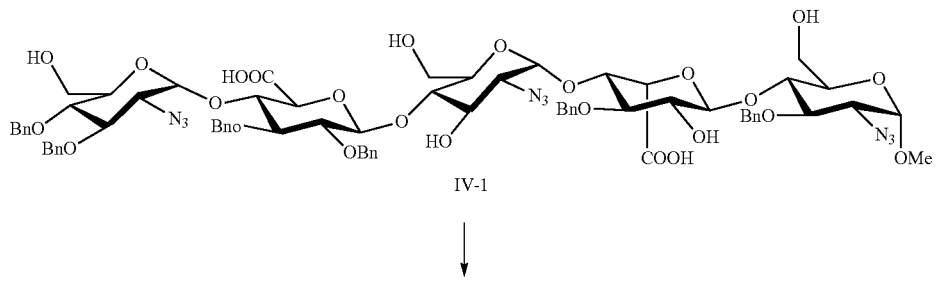

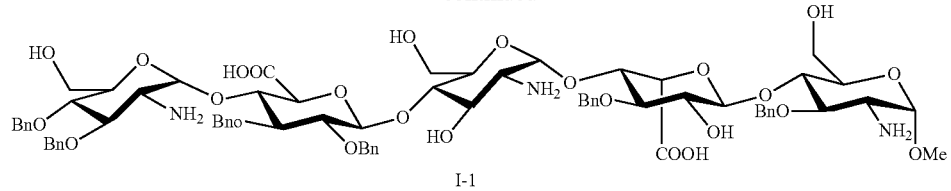

I-1

Under the protection of nitrogen, the pentasccharide compound of formula IV-I (8.0 g) was dissolved in tetrahydrofuran (400 mL), aqueous solution of sodium hydroxide (32 mL, 1.0 M) was added, a solution of trimethylphosphine in tetrahydrofuran (54 mL, 1 M) was added dropwise in ice bath, and then the temperature was slowly raised to room temperature. It was stirred overnight, until the reaction is complete. Dilute hydrochloric acid was added for neutralization, until the pH reaches about 7. It was concentrated under reduced pressure to remove the solvent, in order to obtain 8.8 g compound of formula I-1, in the form of foamy solid. The crude product was subjected to the next reaction without further purification.

HPLC purity: 90%.

ESMS: m/z 1408 [M+1]$^+$, 1406 [M−1]$^−$.

Example 3

Preparation of methyl O-(2-amino-3,4-di-O-benzyl-2-deoxy-α-D-glucopyranosyl)-(1→4)-O-(2,3-di-O-benzyl-β-D-glucopyranuronosyl)-(1→4)-O-(2-amino-2-deoxy-α-D-glucopyranosyl)-(1→4)-O-(3-O-benzyl-α-L-idopyranuronosyl)-(1→4)-2-amino-3-O-benzyl-2-deoxy-α-D-glucopyranoside (I-1)

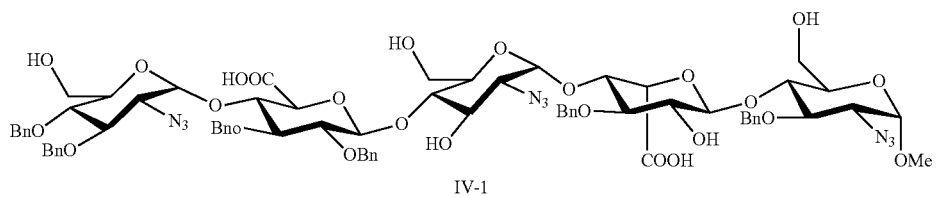

IV-1

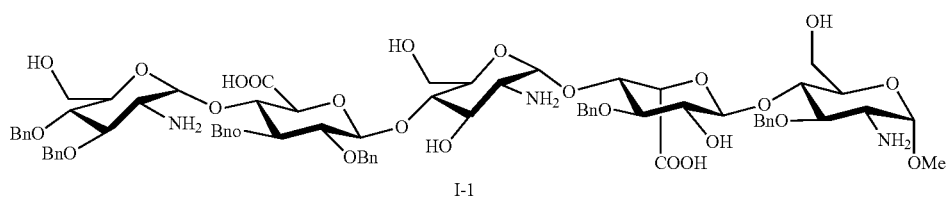

I-1

Under the protection of nitrogen, the pentasccharide compound of formula IV-I (4.0 g) was dissolved in tetrahydrofuran (200 mL), aqueous solution of sodium hydroxide (16 mL, 1.0 M) was added, triphenylphosphine (7.1 g) was added in ice bath, and then the temperature was slowly raised to room temperature. It was stirred overnight, until the reaction is complete. Dilute hydrochloric acid was added for neutralization, until the pH reaches about 7. It was concentrated under reduced pressure to remove the solvent, in order to obtain 11.4 g crude compound of formula I-1, in the form of foamy solid. The crude product was subjected to the next reaction without further purification.

ESMS: m/z 1408 [M+1]$^+$, 1406 [M−1]$^−$.

Example 4

Preparation of methyl O-(2-amino-3,4-di-O-benzyl-2-deoxy-α-D-glucopyranosyl)-(1→4)-O-(2,3-di-O-benzyl-β-D-glucopyranuronosyl)-(1→4)-O-(2-amino-2-deoxy-αD-glucopyranosyl)-(1→4)-O-(3-O-benzyl-α-L-idopyranuronosyl)-(1→4)-2-amino-3-O-benzyl-2-deoxy-α-D-glucopyranoside (I-1)

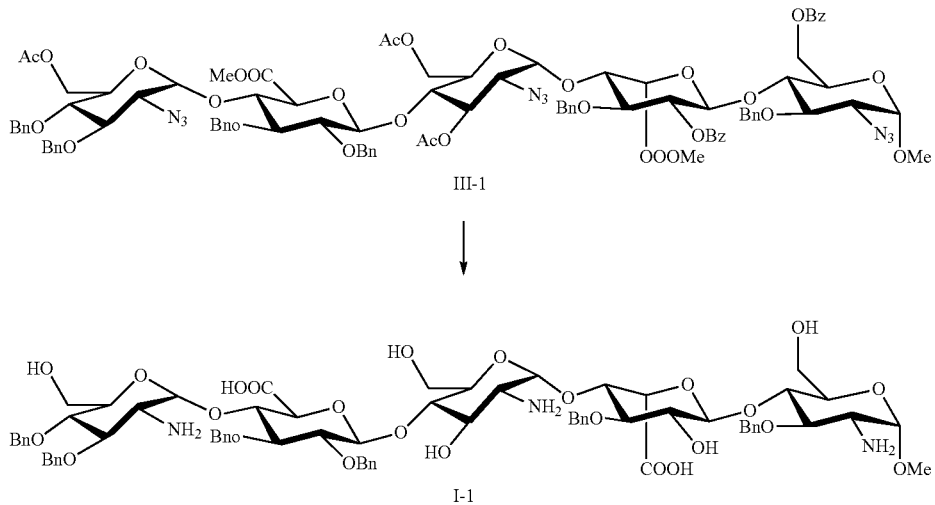

Under the protection of nitrogen, the pentasccharide compound of formula III-I (5.0 g, 2.7 mmol) was dissolved in tetrahydrofuran (200 mL), water (20 mL) was added, a solution of trimethylphosphine in tetrahydrofuran (27 mL, 1 M) was added dropwise in ice bath, and then the temperature was slowly raised to room temperature. It was stirred overnight, until the reaction is complete. Aqueous solution of sodium hydroxide (55 mL, 1.0 M) was added dropwise, and it was stirred at room temperature until the reaction was complete. Dilute hydrochloric acid was added for neutralization, until the pH reaches about 7. It was concentrated under reduced pressure to remove the solvent, in order to obtain 8.4 g crude compound of formula I-1, in the form of foamy solid. The crude product was subjected to the next reaction without further purification.

HPLC purity: 87%.
ESMS: m/z 1408 [M+1]$^+$, 1406 [M−1]$^-$.

Example 5

Preparation of methyl O-(3,4-di-O-benzyl-2-deoxy-6-O-sulfo-2-sulfoamino-α-D-glucopyranosyl)-(1→4)-O-(2,3-di-O-benzyl-β-D-glucopyranuronosyl)-(1→4)-O-(2-deoxy-3,6-di-O-sulfo-2-sulfoamino-α-D-glucopyranosyl)-(1→4)-O-(3-O-benzyl-2-O-sulfo-β-L-idopyranuronosyl)-(1→4)-3-O-benzyl-2-deoxy-6-O-sulfo-2-sulfamino-α-D-glucopyranoside, decasodium salt (II-1)

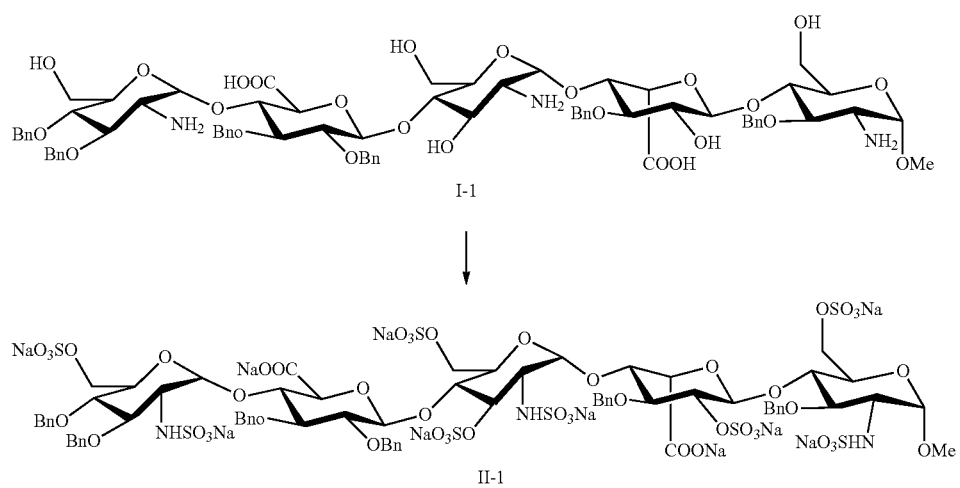

Figure 2:
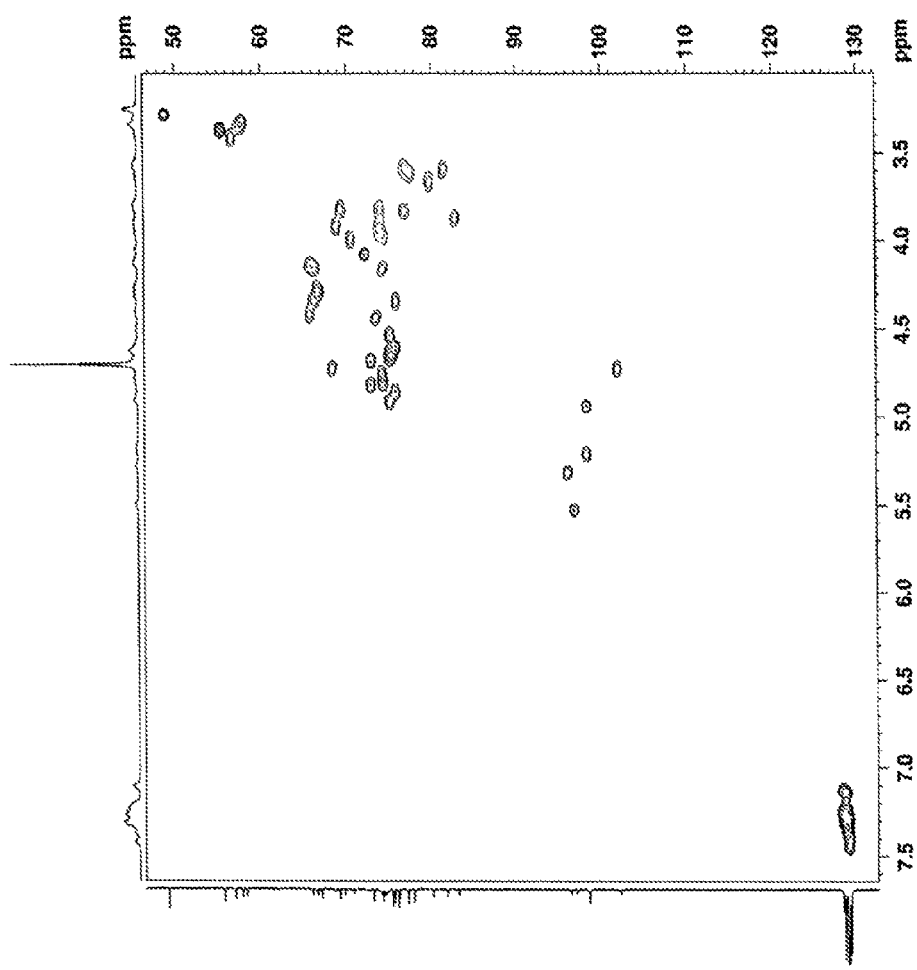
FIG. 2 is the HSQC NMR of the compound of formula II-1 prepared according to Example 5.

Under the protection of nitrogen, the pentasccharide compound of formula I-I (8.8 g) was dissolved in the mixed solvent of pyridine (50 mL) and triethylamine (10 mL), sulfur trioxide-pyridine complex (10 g, 63 mmol) was added. It was stirred overnight at room temperature, until the reaction was complete. Saturated aqueous solution of sodium hydrogen carbonate was added in order to quench the reaction. It was concentrated under reduced pressure to remove the solvent, to obtain a red brown oily product. It was successively purified with ion exchange column and sephadex LH-20 column chromatography. The products were combined and the solvent was removed under reduced pressure, and then dried to obtain 8.2 g compound of formula II-1, in the form of foamy solid. Its $^1$H NMR spectrum is as shown in FIG. 1, and HSQC NMR is as shown in FIG. 2.

ESMS: m/z=1055.5 [M−7Na+5H]$^{2-}$/2, 688.9 [M−9Na+6H]$^{3-}$/3.

$^1$H NMR (400 MHz, D$_2$O): (selected for anomeric H) δ 5.59 (d, J=2.8 Hz, 1H), 5.37 (s, 1H), 5.27 (d, J=7.6 Hz, 1H), 4.93 (according to HSQC NMR), 4.72 (according to HSQC NMR).

Example 6

Preparation of methyl O-(3,4-di-O-benzyl-2-deoxy-6-O-sulfo-2-sulfoamino-α-D-glucopyranosyl)-(1→4)-O-(2,3-di-O-benzyl-β-D-glucopyranuronosyl)-(1→4)-O-(2-deoxy-3,6-di-O-sulfo-2-sulfoamino-α-D-glucopyranosyl)-(1→4)-O-(3-O-benzyl-2-O-sulfo-α-L-idopyranuronosyl)-(1→4)-O-benzyl-2-deoxy-6-O-sulfo-2-sulfamino-α-D-glucopyranoside, decasodium salt (II-1)

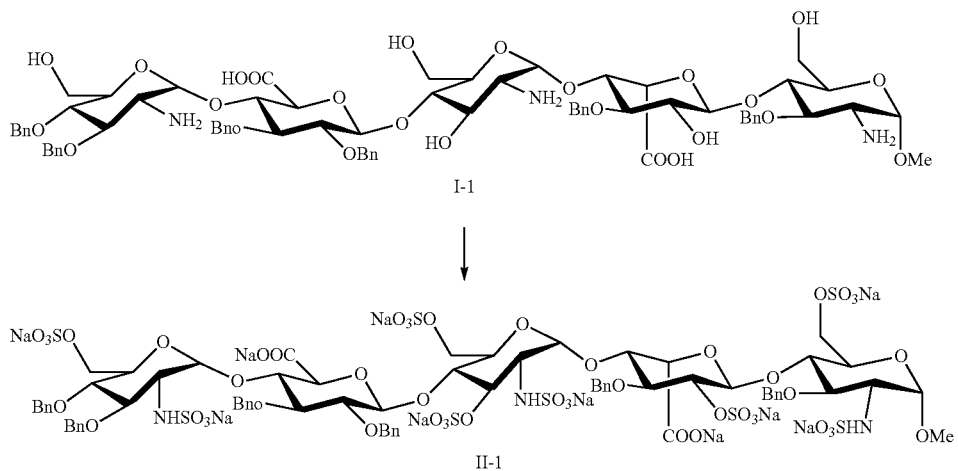

Under the protection of nitrogen, the pentasccharide compound of formula I-I (3.0 g) was dissolved in N,N-Dimethylformamide (100 mL), sulfur trioxide-trimethylamine complex (7.2 g) was added. It was heated to 50° C., until the reaction was complete. Saturated aqueous solution of sodium hydrogen carbonate was added in order to quench the reaction. It was concentrated under reduced pressure to remove the solvent, to obtain a red brown oily product. It was successively purified with ion exchange column and sephadex LH-20 column chromatography. The parts containing sacchrides were combined and the solvent was removed under reduced pressure, and then dried to obtain 2.7 g foamy solid. The foamy solid was dissolved in the mixed solvent of pyridine (50 mL) and triethylamine (10 mL), and sulfur trioxide-pyridine complex (5.1 g) was added. It was stirred overnight at room temperature, until the reaction was complete. Saturated aqueous solution of sodium hydrogen carbonate was added in order to quench the reaction. It was concentrated under reduced pressure to remove the solvent, to obtain a red brown oily product. It was successively purified with ion exchange column and sephadex LH-20 column chromatography, and qualified samples were collected. They were combined and concentrated under reduced pressure to remove the solvent, and were dried to obtain 2.6 g compound of formula II-1, in the form of foamy solid.

Example 7

Preparation of methyl O-(2-deoxy-6-O-sulfo-2-sulfoamino-α-D-glucopyranosyl)-(1→4)-O-(β-D-glucopyranuronosyl)-(1→4)-O-(2-deoxy-3,6-di-O-sulfo-2-sulfoamino-α-D-glucopyranosyl)-(1→4)-O-(2-O-sulfo-α-L-idopyranuronosyl)-(1→4)-2-deoxy-6-O-sulfo-2-sulfoamino-α-D-glucopyranoside, decasodium salt (VI-1, Fondaparinux sodium)

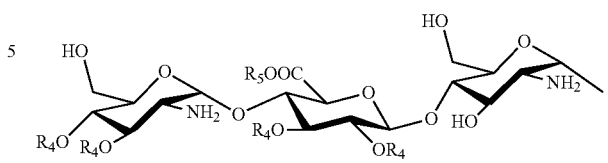

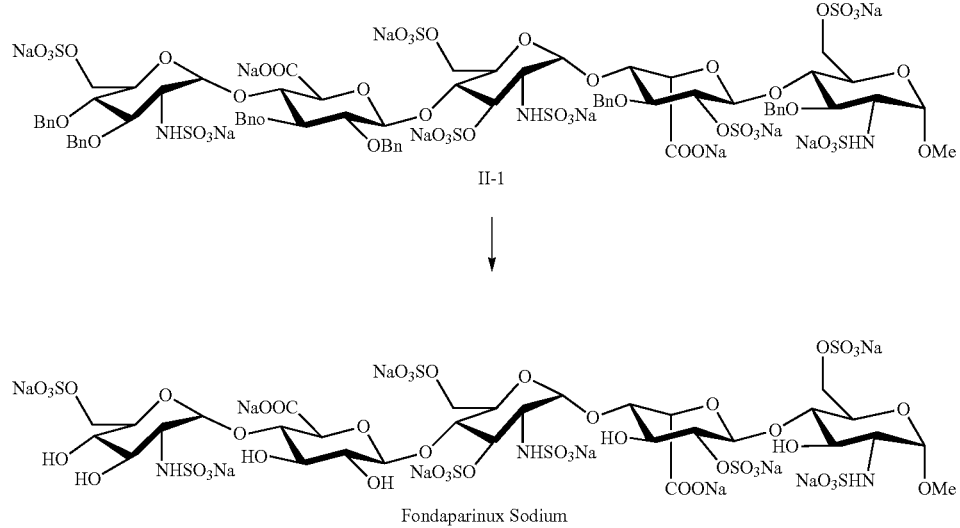

Figure 3:
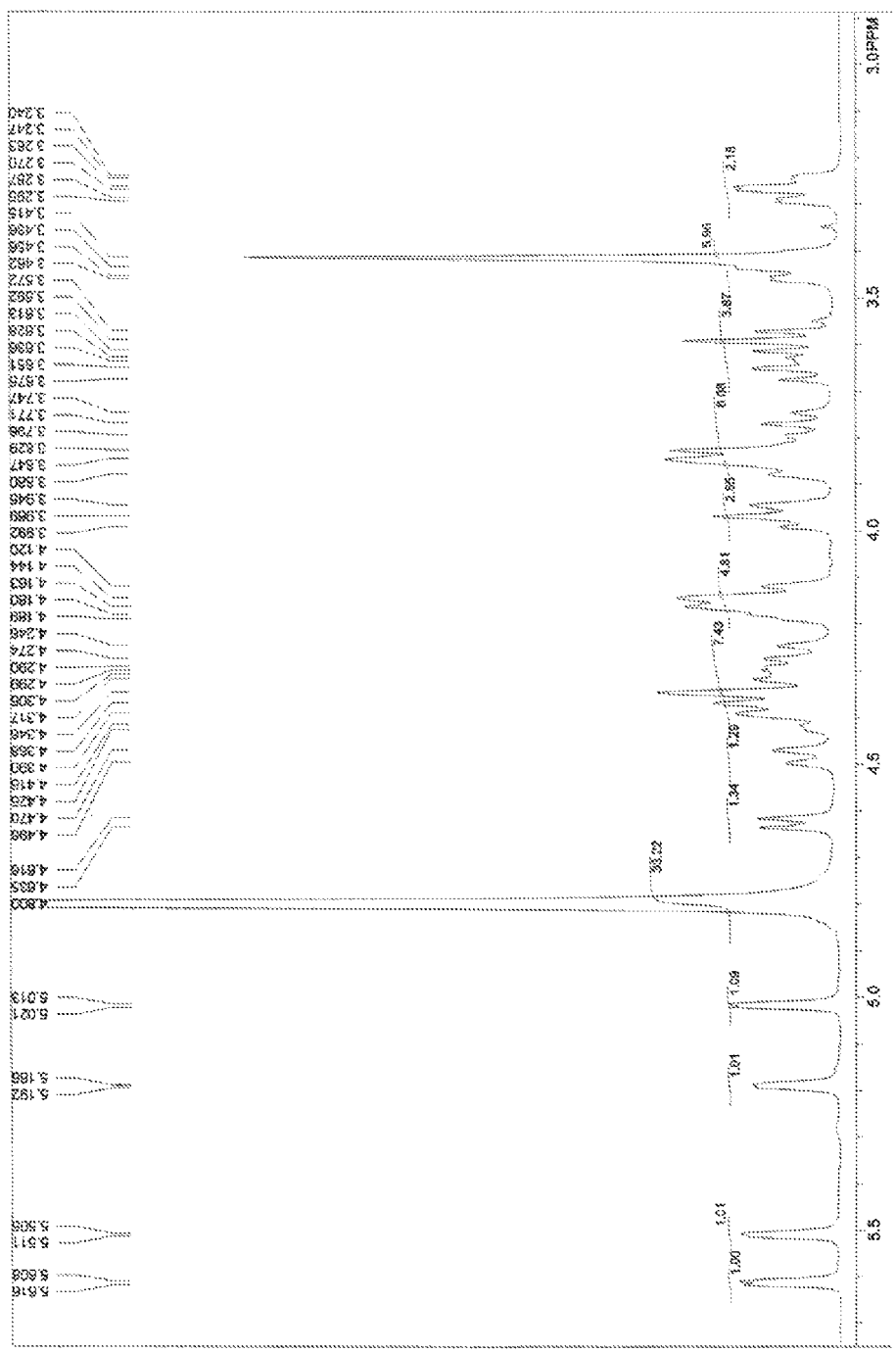
FIG. 3 is the $^1$H NMR of fondaparinux sodium prepared according to Example 7.

8.2 g pentasaccharide of formula II-1 was dissolved in 150 ml mixed solvent of methanol and water (1:1, v/v), 3 g palladium on carbon (10%) was added. The reaction was carried out under hydrogen pressure of 70 psi, until the reaction was complete. The palladium on carbon catalyst was removed by filtration, and the solvent was removed under reduced pressure. It was successively purified with anion exchange column and sephadex G25, in order to obtain 6.4 g final product. Its $^1$H NMR was as shown in FIG. 3.

ESMS: m/z=1727.7 [M+H]$^+$, 1749.7 [M+Na]$^+$.

$^1$H NMR (400 MHz, D$_2$O): (selected for anomeric H) δ 5.61 (d, J=3.2 Hz, 1H), 5.51 (d, J=2.4 Hz, 1H), 5.19 (d, J=2.4 Hz, 1H), 5.02 (d, J=3.2 Hz, 1H), 4.62 (d, J=7.6 Hz, 1H).

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A compound having the following formula I, which can be used as an intermediate for the preparation of heparin pentasaccharide, wherein the configuration of monosaccharide units and the stereochemistry of the connecting bond among each of the monosaccharides is D-glucosyl-α-1,4-D-glucuronosyl-β-1,4-D-glucosyl-α-1,4-L-idoronosyl-α-1,4-D-glucose, wherein the definition of each substituent is as follows:

R represents $C_1$-$C_{20}$ alkyl or substituted alkyl, wherein the alkyl can be either linear alkyl or branched or cyclic alkyl;

$R_4$ represents benzyl or substituted benzyl, and $R_4$ in the same molecular formula represents either identical group or different group;

$R_5$ represents hydrogen ion or alkali metal ion.

2. The compound according to claim 1, characterized in that R is selected from methyl, ethyl, propyl, isopropyl, butyl, isobutyl, tert-butyl, pentyl, benzyl, or cyclohexyl.

3. The compound according to claim 1, characterized in that R is methyl; $R_4$ is benzyl or substituted benzyl; and $R_5$ is hydrogen ion or sodium ion.

4. A compound having the following formula II, which can be used as an intermediate for the preparation of heparin pentasaccharide

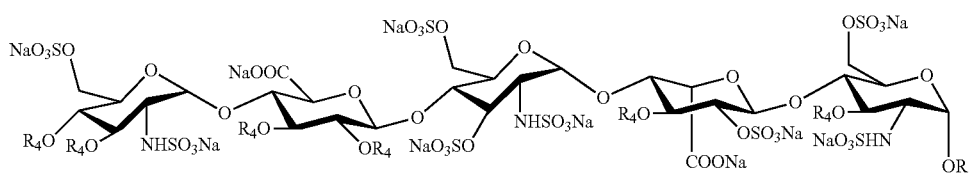

II wherein the configuration of monosaccharide units and the stereochemistry of the connecting bond among each of the monosaccharides is D-glucosyl-α-1,4-D-glucuronosyl-β-1,4-D-glucosyl-α-1,4-L-idoronosyl-α-1,4-D-glucose, wherein the definition of each substituent is as follows:

R represents $C_1$-$C_{20}$ alkyl or substituted alkyl, wherein the alkyl can be either linear alkyl or branched or cyclic alkyl;

$R_4$ represents benzyl or substituted benzyl, and $R_4$ in the same molecular formula represents either identical group or different group.

5. The compound according to claim 4, characterized in that R is selected from methyl, ethyl, propyl, isopropyl, butyl, isobutyl, tert-butyl, pentyl, benzyl, or cyclohexyl.

6. The compound according to claim 4, characterized in that R is methyl; and $R_4$ is benzyl or substituted benzyl.

7. A process for the preparation of the compound of formula I according to claim 1, characterized in that the process comprises the following steps:
   a) firstly, treating the fully protected pentasaccharide compound of the following formula III with sodium hydroxide, wherein R represents $C_1$-$C_{20}$ alkyl or substituted alkyl, wherein the alkyl can be either linear alkyl or branched or cyclic alkyl; $R_1$ represents $C_1$-$C_{20}$ alkyl, substituted alkyl, hydrogen ion, sodium ion, wherein the alkyl can be either linear alkyl or branched or cyclic alkyl, $R_1$ in the same molecular formula represents either identical group or different group; $R_2$ represents linear or branched aliphatic acyl or aryl acyl, $R_2$ in the same molecular formula represents either identical group or different group; $R_3$ represents azido group; $R_4$ represents benzyl or substituted benzyl, $R_4$ in the same molecular formula represents either identical group or different group; $R_5$ is hydrogen ion or sodium ion;

b) secondly, treating the compound of formula IV with a reductant, i.e. the group $R_3$ is reduced to amino group, in order to obtain the compound of formula I.

8. The process according to claim 7, characterized in that $R_2$ in the compound of formula III is selected from acetyl, 4-oxovaleryl, and benzoyl; and wherein the acid is preferably hydrochloric acid.

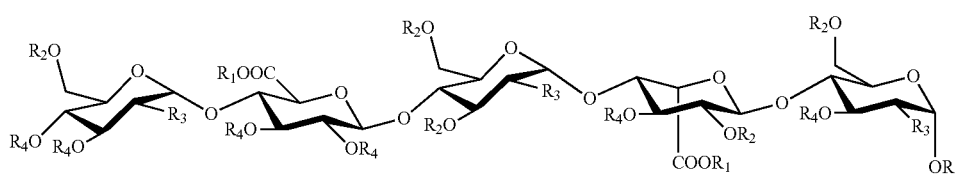

III such that the compound of formula III is subjected to ester hydrolysis, in order to obtain the compound having the following formula IV wherein $R_5$ is sodium ion, alternatively, the compound is subjected to hydrolysis and subsequent acid neutralization, in order to obtain the compound having the following formula IV wherein $R_5$ is hydrogen ion, 9. The process according to claim 7, wherein the compound of formula IV is subjected to reduction after separation and purification.

10. A process for the preparation of the compound according to claim 1 having the following formula I:

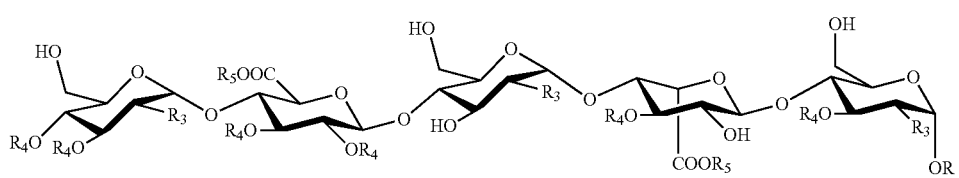

IV

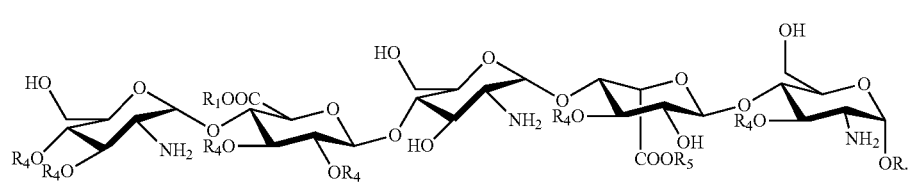

comprising the following steps:
a) firstly, treating the fully protected pentasaccharide compound of formula III with a reductant,

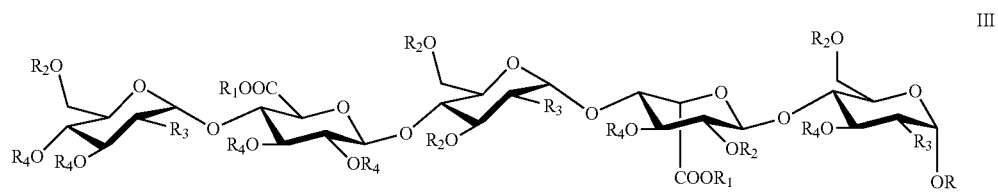

reducing $R_3$ group into amino group, in order to obtain the compound of the following formula V,

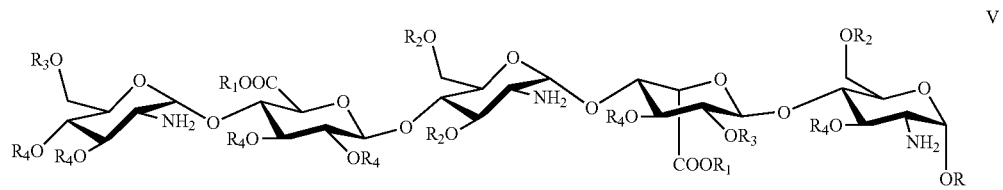

wherein R represents $C_1$-$C_{20}$ alkyl or substituted alkyl, wherein the alkyl can be either linear alkyl or branched or cyclic alkyl; $R_1$ represents $C_1$-$C_{20}$ alkyl, substituted alkyl, hydrogen ion, sodium ion, wherein the alkyl can be either linear alkyl or branched or cyclic alkyl, $R_1$ in the same molecular formula represents either identical group or different group; $R_2$ represents linear or branched aliphatic acyl or aryl acyl, $R_2$ in the same molecular formula represents either identical group or different group; $R_4$ represents benzyl or substituted benzyl, $R_4$ in the same molecular formula represents either identical group or different group;

b) secondly, treating the compound of formula V with sodium hydroxide, such that the compound of formula V is subjected to ester hydrolysis, in order to obtain the compound of formula I wherein $R_5$ is sodium ion, alternatively, it is subjected to ester hydrolysis and subsequent acid neutralization, in order to obtain the compound of formula I wherein $R_5$ is hydrogen ion.

11. The process according to claim 10, characterized in that $R_2$ in the compound of formula V is selected from acetyl, 4-oxovaleryl, and benzoyl; and wherein the acid is preferably hydrochloric acid.

12. The process according to claim 7, characterized in that the reductant is selected from trimethylphosphine, triethylphosphine, tributylphosphine, triphenylphosphine, or hydrogen sulfide.

13. A process for the preparation of the compound of formula II:

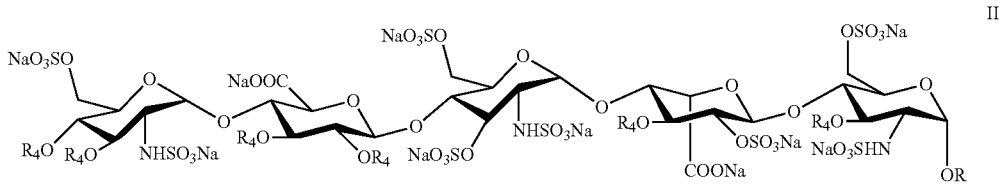

characterized in that treating the compound having the following formula I:

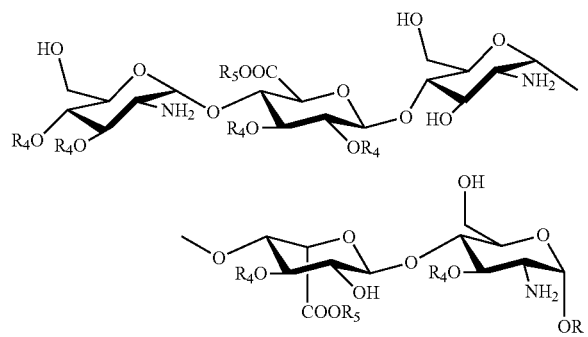

I with a sulfating reagent, and treating the obtained crude product with sodium ion exchange resin, in order to obtain the compound of formula II; wherein the sulfating reaction can be carried out in a single step or in several steps.

14. The process according to claim 13, characterized in that the sulfating agent is selected from sulfur trioxide-pyridine complex, sulfur trioxide-trimethylamine complex, sulfur trioxide-triethylamine complex, or gaseous sulfur trioxide.

15. A process for the preparation of heparin pentasaccharide compound of formula VI, characterized in that treating the compound according to claim 4 having the following formula II:

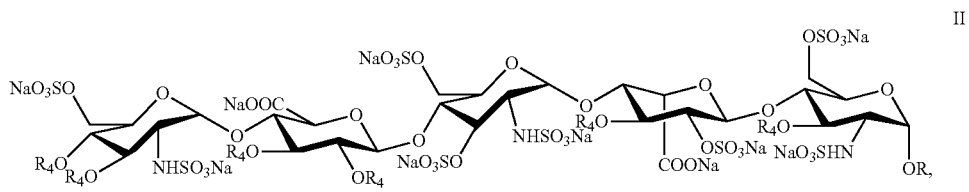

II with a catalyst, palladium hydroxide or palladium on carbon, under hydrogen condition, such that all $R_4$ groups of the compound of formula II are removed, in order to obtain heparin pentasaccharide compound according to formula VI

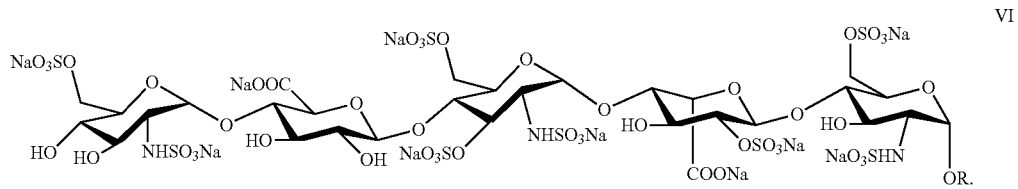

VI

16. The process according to claim 7, wherein the heparin pentasaccharide is fondaparinux sodium.

17. The process according to claim 10, characterized in that the reductant is selected from trimethylphosphine, triethylphosphine, tributylphosphine, triphenylphosphine, or hydrogen sulfide.

18. The process according to claim 13, wherein the heparin pentasaccharide is fondaparinux sodium.

* * * * *